US00PP09957P

United States Patent [19]

Brouwer

[11] Patent Number: Plant 9,957

[45] Date of Patent: Jul. 8, 1997

[54] SPATHIPHYLLUM PLANT NAMED JETTY

[75] Inventor: Wim A. J. Brouwer, Nootdorp, Netherlands

[73] Assignee: Milestone Agriculture Inc., Apopka, Fla.

[21] Appl. No.: 627,607

[22] Filed: Apr. 4, 1996

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—C. A. Whealy

[57] ABSTRACT

A distinct cultivar of Spathiphyllum plant named Jetty, characterized by its numerous leaves and side shoots giving a dense, full appearance; leaves are large and have an undulating margin and wavy appearance, spathe is yellow white in color before unrolling; numerous large flowers that are positioned 10 to 20 cm above the foliage on strong and erect peduncles; pure white cupped spathe that curves over the top of the spadix; and long-lasting flowers.

1 Drawing Sheet

The present invention relates to a new and distinct cultivar of Spathiphyllum plant, botanically known as Spathiphyllum, and hereinafter referred to by the cultivar name Jetty.

The new cultivar is a product of a planned and controlled breeding program conducted by the inventor in Nootdorp, The Netherlands. The new cultivar originated from a delibrate cross by the inventor between the Spathiphyllum cultivar Illusion (U.S. Plant patent application Ser. No. 08/627,460) as the female or seed parent and the Spathiphyllum cultivar Auslese (not patented) as the male or pollen parent. The cultivar Jetty was discovered and selected by the inventor as a plant within the progeny of the stated cross in a controlled environment in Nootdorp, The Netherlands.

Asexual propagation by division of the new cultivar at Nootdorp, The Netherlands, has shown that the unique features of this new Spathiphyllum plant are stable and reproduced true to type in successive generations of asexual propagation.

The new Spathiphyllum has not been observed under all possible environmental conditions. The phenotype may vary somewhat with variations in environment such as temperature and light intensity, without, however, any variance in genotype. The following observations, measurements and comparisons describe plants grown in Kwintsheul, The Netherlands, in 14-cm containers in a glass greenhouse with an average day temperature of 22 C., and average night temperature of 20 C., and a light level of 200 to 225 lux.

The following traits have been repeatedly observed and are determined to be the unique characteristics of Jetty. These characteristics in combination distinguish Jetty as a new and distinct cultivar:

1. Numerous leaves and side shoots give a dense full appearance.
2. Leaves are large and have an undulating, wavy margin and are held at a 80° to 90° angle to the petiole, slightly drooping.
3. Spathe is yellow white in color before unrolling.
4. Numerous large flowers that are positioned 10 to 20 cm above the foliage on strong and erect peduncles.
5. Pure white cupped spathe that curves over the top of the spadix.
6. Long-lasting flowers.

The new Spathiphyllum can be compared to its seed parent cultivar, the cultivar Illusion and is different from the cultivar Illusion in the following characteristics:

1. Plants of the cultivar Jetty have more leaves and side shoots and therefore a denser plant habit than plants of the cultivar Illusion.

2. Mature leaves of plants of the cultivar Jetty are glossier than mature leaves of plants of the cultivar Illusion.
3. Leaves of plants of the cultivar Jetty have an undulating margin giving leaves a wavy appearance. Leaves of plants of the cultivar Illusion are flat and the leaf margin is not undulating.
4. Plants of the cultivar Jetty flower later than plants of the cultivar Illusion.
5. Plants of the cultivar Jetty have longer flower peduncles than plants of the cultivar Illusion and flowers on plants of the cultivar Jetty are positioned higher above the foliage compared to plants of the cultivar Illusion.
6. Before unrolling, the spathe color on plants of the cultivar Jetty is yellow white and the spathe color on plants of the cultivar Illusion is white.

The new Spathiphyllum can be compared to its pollen parent cultivar, the cultivar Auslese and is different from the cultivar Auslese in the following characteristics:

1. Plants of the cultivar Jetty have more leaves and side shoots and therefore a denser plant habit than plants of the cultivar Auslese.
2. Plants of the cultivar Jetty are more vigorous than plants of the cultivar Auslese.
3. Plants of the cultivar Jetty have larger leaves and flowers than plants of the cultivar Auslese.
4. Leaves of the plants of the cultivar Jetty have an undulating margin giving leaves a wavy appearance. Leaves of plants of the cultivar Auslese are flat and the leaf margin is not undulating.
5. Leaves of plants of the cultivar Jetty have more horizontal leaves, less drooping, than plants of the cultivar Auslese.
6. Plants of the cultivar Jetty flower later than plants of the cultivar Auslese.
7. The spathe on plants of the cultivar Jetty is cupped whereas the spathe on plants of the cultivar Auslese is straight and not curved.
8. Before unrolling, the spathe color on plants of the cultivar Jetty is yellow white and the spathe color on plants of the cultivar Auslese is white.

The new Spathiphyllum is similar to the cultivar Viscount. The new Spathiphyllum differs from the cultivar Viscount in the following characteristics:

1. Plants of the cultivar Jetty have more side shoots and are denser in appearance than plants of the cultivar Viscount.
2. Plants of the cultivar Jetty have larger leaves than plants of the cultivar Viscount.
3. Leaves of the plants of the cultivar Jetty have an undulating margin giving leaves a wavy appearance. Leaves of plants of the cultivar Viscount are flat and the leaf margin is not undulating.

4. Plants of the cultivar Jetty have shorter flower peduncles that are upright and strong which position flowers above the foliage. Plants of the cultivar Viscount have longer flower peduncles and peduncles are weak and tend to lean outward which position the flowers on the outside of the plant rather than above the foliage.

5. Before unrolling, the spathe color on plants of the cultivar Jetty is yellow white and the spathe color on plants of the cultivar Viscount is white.

The accompanying colored photograph illustrates the overall appearance of the new cultivar, showing the colors as true as it is reasonably possible to obtain in colored reproduction of this type. The photograph comprises a top perspective view of a typical potted plant of Jetty.

In the following description, color references are made to The Royal Horticultural Society Colour Chart except where general terms of ordinary dictionary significance are used.

Botancial classification: Spathiphyllum cultivar Jetty.

Parentage:

*Seed or female parent.*—Spathiphyllum cultivar Illusion (U.S. Plant Patent Applied For).

*Pollen or male parent.*—Spathiphyllum cultivar Auslese (not patented).

Propagation: Divisions and by tissue culture.

Plant description:

*Plant shape.*—Upright, inverted triangle, symmetrical.

*Growth habit.*—Erect when young, becoming outwardly arching as leaves develop. Numerous side shoots give plants a full, dense appearance. Appropriate for 14-cm containers.

*Plant height.*—50 to 60 cm from soil level to top of leaf plane.

*Plant vigor.*—Moderate.

*Crop time.*—Twenty-four weeks are usually require from planting of a young plant to a finished 14-cm container.

*Rooting habit.*—Freely branching, numerous fleshy roots with finer lateral roots.

*Foliage description.*—Leaf shape: Young: Narrowly ovate. Mature: Ovate. Leaf length: 28.5 to 31 cm. Leaf width: 13 to 16 cm. Margin: Entire and undulating. Leaf surface: Wavy. Leaf tip: Acuminate. Leaf base: Obtuse. Leaf aspect: Mature leaves held at a 80° to 90° angle to petiole. Leaves curve downward, slightly drooping. Leaf texture: Leathery, smooth, glabrous. Leaf color: Young, top side: 137B, glossy. Young, under side: 137C. Mature, top side: 137A, glossy. Mature, under side: 137C. Petiole length, primary shoot: 45 to 60 cm. Petiole diameter, primary shoot, just below geniculum: About 4 mm. Geniculum diameter, primary shoots: About 5 mm. Petiole wing, primary shoots: Apparent on lower 60% of mature leaf petiole. Petiole color: Young: 137B/137C. Mature: Winged area: 137A. Above winged area: 137A. Geniculum: 137C. Venation: Top side: 137A, sunken. Under side: Lighter than 137C, prominent.

Flower description:

*Flower arrangement.*—Cupped spathe with spadix held 10 to 20 cm above the foliage. Flowers arise from leaf axils.

*Flower longevity.*—Flowers are long-lasting, generally maintaining white color for 8 to 12 weeks on the plant depending on light and temperature levels.

*Spathe.*—Shape: Ovate. Size: Length: About 14 cm. Width: About 9 cm. Aspect: Curves over the spadix. Color: Before unrolling: Yellow white (8D). Open flower: White (155D) and shiny.

*Spadix.*—Size: Length: About 7 cm. Diameter: About 12 mm. Color: 8D.

*Peduncle.*—Aspect: Strong and erect. Size: Length: 60 to 70 cm. Diameter: About 5 mm. Color: 137A.

Disease resistance: No resistance to disease has been noted.

Seed development: Seed development is rarely observed.

It is claimed:

1. A new and distinct cultivar of Spathiphyllum plant named Jetty, as illustrated and described.

* * * * *

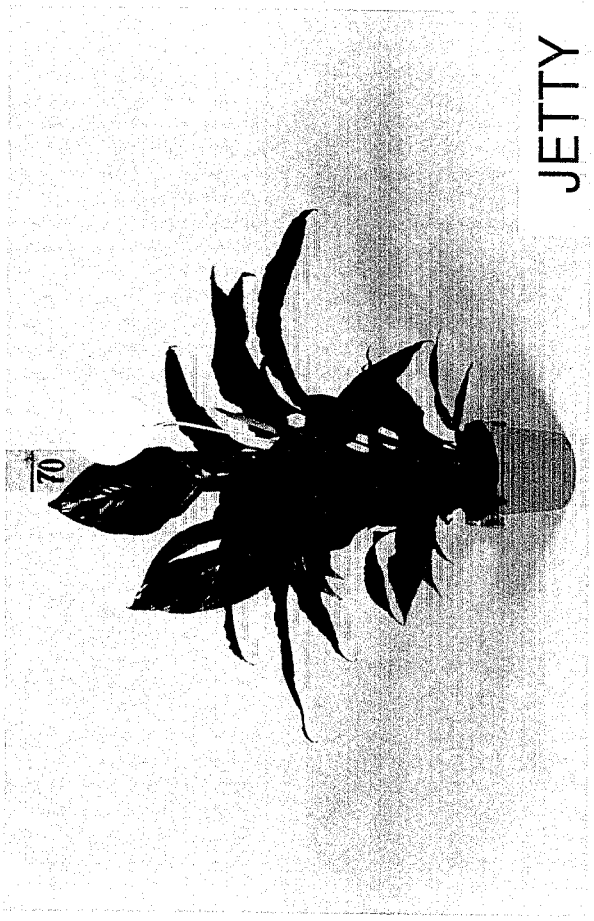
70
JETTY